United States Patent [19]
Rao et al.

[11] Patent Number: 6,050,127
[45] Date of Patent: Apr. 18, 2000

[54] MICRO-BALL IMPACT TESTER

[75] Inventors: Mukund Channagiri Rao, Oklahoma City; Harold Weaver Pexton, Moore, both of Okla.

[73] Assignee: Seagate Technology, Inc., Scotts Valley, Calif.

[21] Appl. No.: 09/350,839

[22] Filed: Jul. 9, 1999

Related U.S. Application Data

[63] Continuation of application No. 08/956,659, Oct. 23, 1997.

[51] Int. Cl.$^7$ ..................................................... G01N 3/30
[52] U.S. Cl. ......................................... 73/12.13; 73/12.06
[58] Field of Search ............................... 73/12.01, 12.02, 73/12.06, 12.07, 12.09, 12.11, 12.12, 12.13, 12.14, 81, 82

[56] References Cited

U.S. PATENT DOCUMENTS

| | | |
|---|---|---|
| 3,896,657 | 7/1975 | Brandt et al. . |
| 4,006,626 | 2/1977 | Ruzicka et al. . |
| 4,375,762 | 3/1983 | Yanagisawa et al. . |
| 4,885,933 | 12/1989 | Heistand et al. . |

OTHER PUBLICATIONS

Y. Tirupataiah, B. Venkataraman and G. Sundarajan, The Nature of the Elastic Rebound of a Hard Ball Impacting on Ductile Metallic Target Materials, Materials Science and Engineering, vol. A124, pp. 133–140, 1990.

G. Sundarajan and P.G. Shewmon, The Use of Dynamic Impact Experiments in the Determination of the Strain Rate Sensitivity of Metals and Alloys, Acta Metallurgica, vol. 31, pp. 101–109, 1983.

I.M. Hutchings, Strain Rate Effects in Microparticle Impact, Journal of Physics D (Applied Physics), vol. 10, pp. L179–L–184, 1977.

*Primary Examiner*—Max Noori
*Attorney, Agent, or Firm*—Crowe & Dunlevy

[57] ABSTRACT

An apparatus and method for impact response testing of materials such as magnetic discs of a disc drive. The apparatus of the present invention supports a target disc in cooperative relationship with a sub-millimeter impact test ball such that the test ball can be dropped on selected portions of the target disc from selected heights above the target disc. The apparatus permits the method of observing the characteristics of a detent made in the target disc, by use of a high resolution surface profiler, and interpolating the observed characteristics to analytical standards which, for a given test ball size and drop height, indicate the dynamic hardness of the target disc at that test location. A vacuum is used to support the test ball above the disc, and a vacuum release valve is provided to negate the vacuum and release the test ball.

5 Claims, 4 Drawing Sheets

MICRO-BALL IMPACT TESTER

This application is a continuation of Ser. No. 08/956,659 filed Oct. 23, 1997.

FIELD OF THE INVENTION

The present invention relates generally to the field of material physical property characterization and more particularly, but not by way of limitation, to an impact tester using a sub-millimeter size impact ball to facilitate determination of dynamic hardness and impact response of a magnetic disc of the type used in a conventional disc drive assembly.

BACKGROUND OF THE INVENTION

Disc drives enable users of computer systems to store and retrieve vast amounts of data in a fast and efficient manner. The data are stored on one or more circular discs having a selectively magnetizable media accessed by a corresponding array of read/write heads of a controllably positionable actuator.

A leading failure mode of disc drives is mechanical failure of the magnetic media due to contact between the discs and actuator and/or heads when the disc drives are subjected to external mechanical shocks. It is generally recognized that resistance to such failures is an inherent material property of the media, favorably correlated to media hardness as indicated by impact response. Thus, by specifying an acceptable dynamic hardness threshold for a magnetic disc, such failures can be substantially minimized. Measurement and characterization of the impact response of a magnetic disc, to the extent that it is indicative of dynamic hardness, is thus a worthy objective in support of a disc drive manufacturer's quality and reliability goals.

Impact methods using spherical balls have been used for a number of years to determine the hardness of various materials. Extensive efforts have been extended in developing analytical interpolation approaches which compare the characteristic response of tested materials to the response of a known material. These efforts have lead to the successful development of relatively aggressive test methods using metallic balls several millimeters in diameter which impact the target material at velocities of several meters per second, typically leaving craters several micrometers deep. Such conditions as these are relatively easy to control and the characteristic responses are relatively easy to measure and correlate.

The present state of the art, however, is ill-suited to the testing of magnetic disc media. The impact conditions of the existing art are prohibitively aggressive for purposes of evaluating the physical properties of the top surface layers of a disc drive disc, as these layers are, collectively, typically less than a micrometer thick. Because the magnitude of a detent in the target material created by an impacting ball is directly proportional to the amount of energy in the falling ball, less aggressive impact conditions necessitate the use of lighter and smaller balls and lower drop heights in order to evaluate such media substrates. However, the lack of precision in the prior art introduces significant error in the repeatability of detent characteristics, where the characteristics of concern are measured in terms of angstroms. That is, at the very low drop heights required to make indentations as shallow as described here, small errors in height and non smooth releases can cause large variations in crater depths. Therefore, accurate height positioning and smooth release are critical. Prior art impact testers introduce excessively deep craters and excessive amounts of variability with regard to ball release dynamics, ball positioning, disc support and the like, making characterization of physical properties of magnetic media impractical. More importantly, it has not been possible to make sub-micrometer deep indents using the larger balls even at very low drop heights because of too much energy in balls greater in size than one millimeter even at one to two millimeter drop heights.

Accordingly, there is a need for advancements in the art whereby the physical properties of highly sensitive materials, such as the magnetic media of disc drive discs, can be precisely and reliably determined.

SUMMARY OF THE INVENTION

The present invention provides an apparatus and method for impact response testing of highly sensitive materials, such as magnetic discs of a disc drive.

In accordance with the preferred embodiment of the present invention, an impact ball test apparatus is provided to support a target material in cooperative relationship with an impact ball so that the ball can be dropped on selected portions of the target material and from selected heights above the target material. The apparatus permits subsequent observation, such as by the use of a surface profilometer or a high power microscope, of the characteristics of a detent made in the target material by the impacting ball, and interpolating the observed characteristics to analytical standards which, for a given ball size, weight, and drop height, indicate the dynamic hardness of the target material at the test location.

Generally, the apparatus comprises a base having a platform which in turn supports a material holder and a ball drop fixture, the material holder supporting the target material and the ball drop fixture supporting a test ball. A vacuum source operably connected to the ball drop fixture provides a suction pressure enabling the support of the test ball. A vacuum release valve is provided to negate the suction pressure to release the test ball.

These and various other features as well as advantages which characterize the present invention will be apparent from a reading of the following detailed description and a review of the associated drawings.

DETAILED DESCRIPTION

Figure 1:
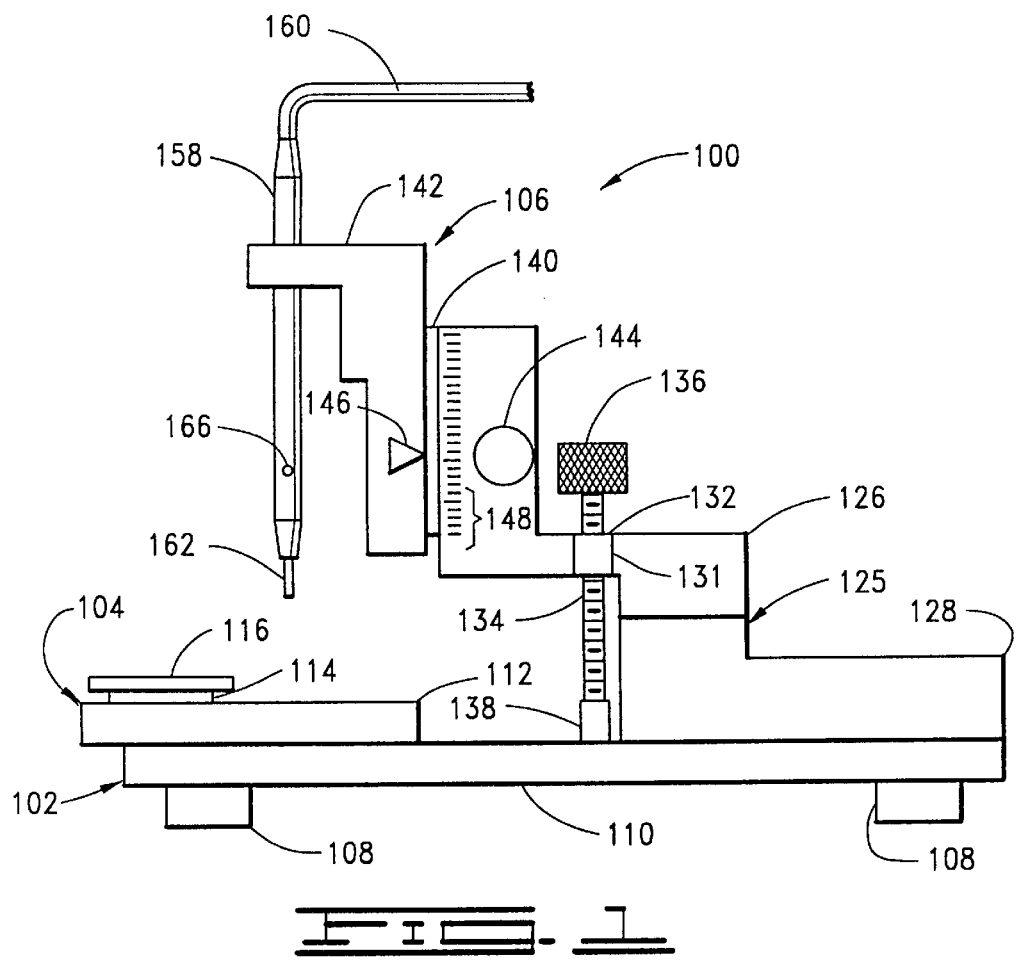
FIG. 1 is a side elevational view of an impact tester constructed in accordance with a preferred embodiment of the present invention.

Referring to the drawings in general and in particular to FIG. 1, shown therein is an impact tester 100 constructed in accordance with a preferred embodiment of the present invention. A base assembly 102 supports a disc holder assembly 104 and a ball drop fixture assembly 106. The base assembly 102 includes a number of support feet 108 which support a rigid platform 110. The support feet 108 are threadingly attached (not shown) to the support plate 110 in a conventional manner to permit independent adjustment so as to level the platform 110 upon the plurality of feet 108. The disc holder assembly 104 has a swivel plate 112 that is articulately supported by the platform 110. The swivel plate 112 supports a bearing assembly 114 which, in turn, rotationally supports a disc plate 116.

Figure 2:
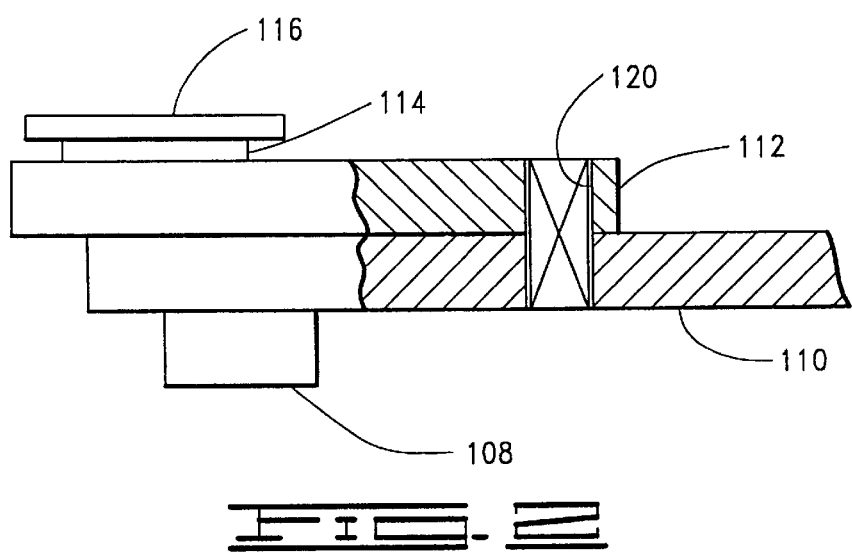
FIG. 2 is a partial cross-sectional view of a portion of the impact tester of FIG. 1, showing in detail the articulated connection of the swivel plate and the platform of the impact tester.

FIG. 2 shows a portion of the impact tester 100 of FIG. 1, wherein it will be observed that the swivel plate 112 is journalled with the platform 110 by a roller bearing assembly 120. In this manner the swivel plate 112 is supported by the top surface of the platform 110 at various angular positions provided by the articulation of the swivel plate 112 relative the fixed platform 110. This articulation allows the testing of selected portions of a disc, as is discussed below.

Figure 3:
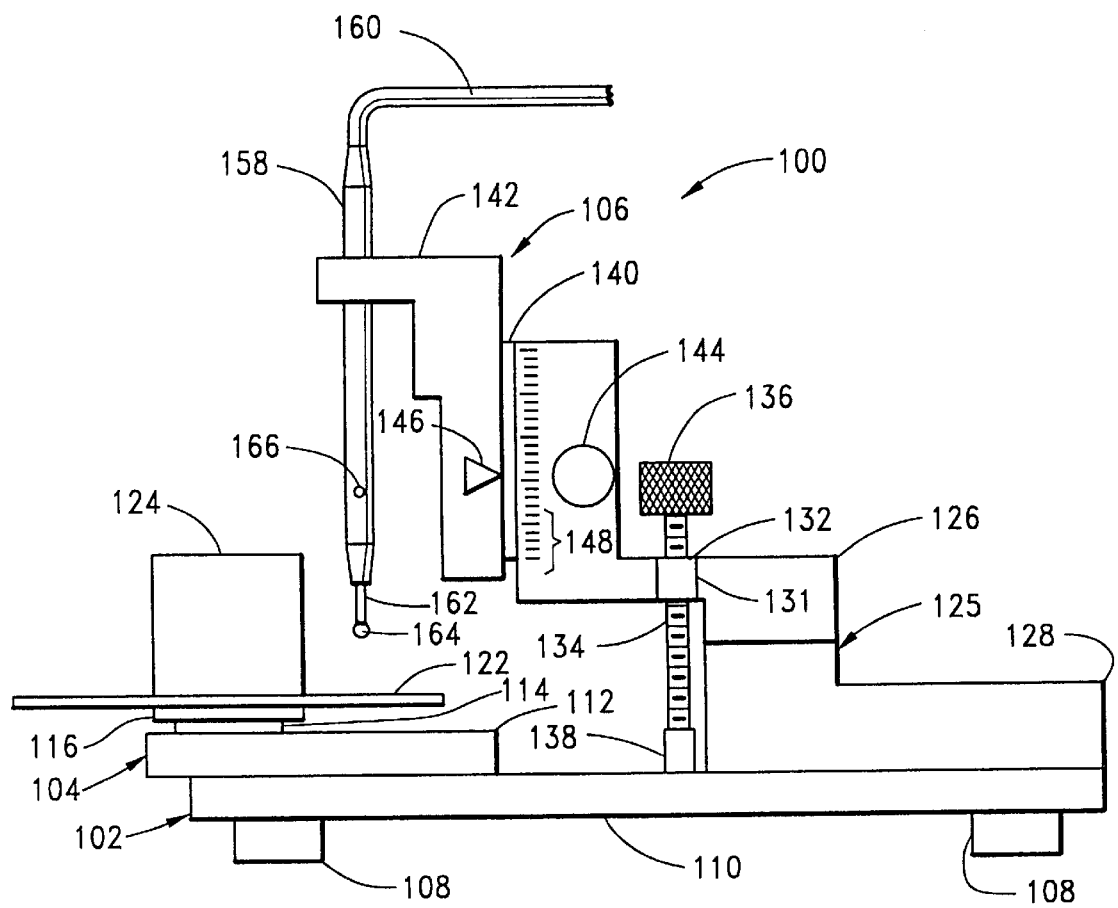
FIG. 3 is a side elevational view of the impact tester of FIG. 1, further illustrating an impact ball loaded in the ball fixture assembly and a target disc supported on the disc holder assembly of the impact tester.

Turning now to FIG. 3, shown therein is a target disc 122 supported by the disc plate 116 in a position suitable for testing. It will be noted that the disc plate 116 supports only a central hub portion of the target disc 122, the portion corresponding to the diameter of a conventional disc spacer (not shown) as conventionally used in a disc drive assembly (not shown). There is no supporting contact of the target disc 122 beneath the locations where testing occurs. To prevent undesirable deflection or vibration of the target disc 122 during testing, an anchor weight 124 is placed on the target disc 122. The weight 124, having a diameter the size of a conventional disc spacer (not shown), covers the central hub portion of the target disc 122.

Figure 4:
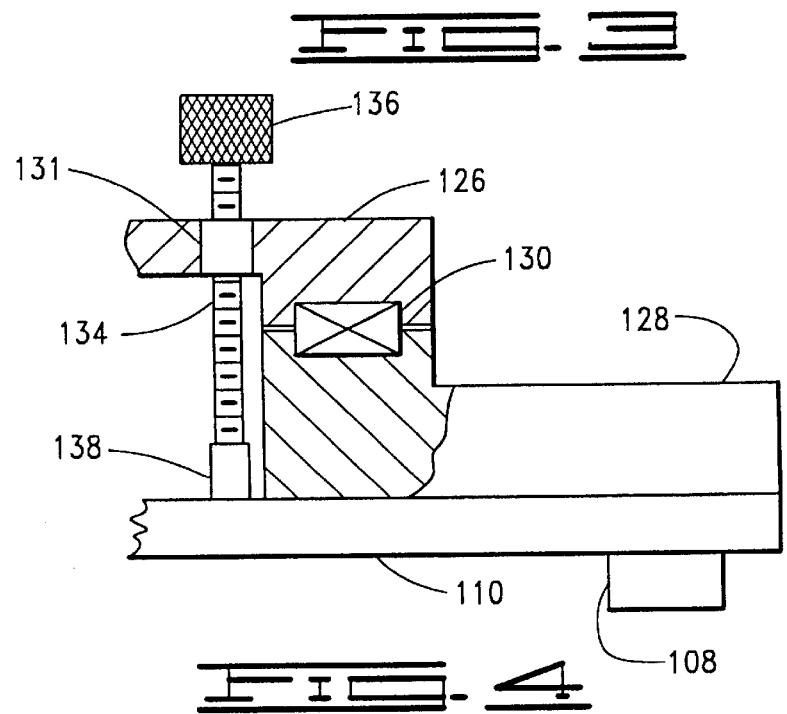
FIG. 4 is a partial cross-sectional view of a portion of the impact tester of FIG. 1, showing in detail the articulated connection of the upper and lower bases of the impact tester.

Returning now to FIG. 1, it will be understood that the ball drop fixture assembly 106 cooperates with the disc holder assembly 104 previously described to permit the impact test of the present invention at any desired location of the target disc 122 (hereinafter referred to as "desired target location"). The ball drop fixture assembly 106 is supported by an articulating fixture base assembly 125 having an upper base 126 and a lower base 128. FIG. 4 shows a portion of the ball drop fixture assembly 106, illustrating a bearing assembly 130 supported by the lower base 128 which, in turn, supports the upper base 126. In this manner it will be understood that the upper base 126 is articulately supported upon the lower base 128.

Turning back to FIG. 1, it will be noted that an extended portion 131 of the upper base 126 forms a threaded passage 132 through which is disposed a threaded shaft 134. Turning of a knurled knob 136 attached to the upper end of the shaft 134 thereby threadingly advances the shaft 134 upward or downward, depending on the direction of rotation. A gripping brake 138 is axially pinned in a conventional manner, such as by riveting, to the distal end of the shaft 134. Hence, rotation of the knob 136 so as to affect downward advancement of the shaft 134 will eventually result in the brake 138 pressingly engaging the platform 110. Friction produced by this pressing engagement will prevent further rotation of the brake 138, and additional rotation of the knob 136 thereafter imparts a compressive load on the shaft 134 which locks the upper base 126 relative the lower base 128. The segmented construction allowing independent rotation of the shaft 134 relative the brake 138 minimizes the effect of lockingly engaging against the platform 110.

The upper base 126 furthermore supports a precision slide 140 which, in turn, supports a vertically positionable support head 142. The vertical position of the support head 142 is responsive to rotation of a knurled knob 144 as further discussed below. The vertical position of the support head 142 is indicated by a reference pointer 146 attached to the support head 142 in cooperation with a series of index marks 148 on the stationary upper base 126.

Figure 5:
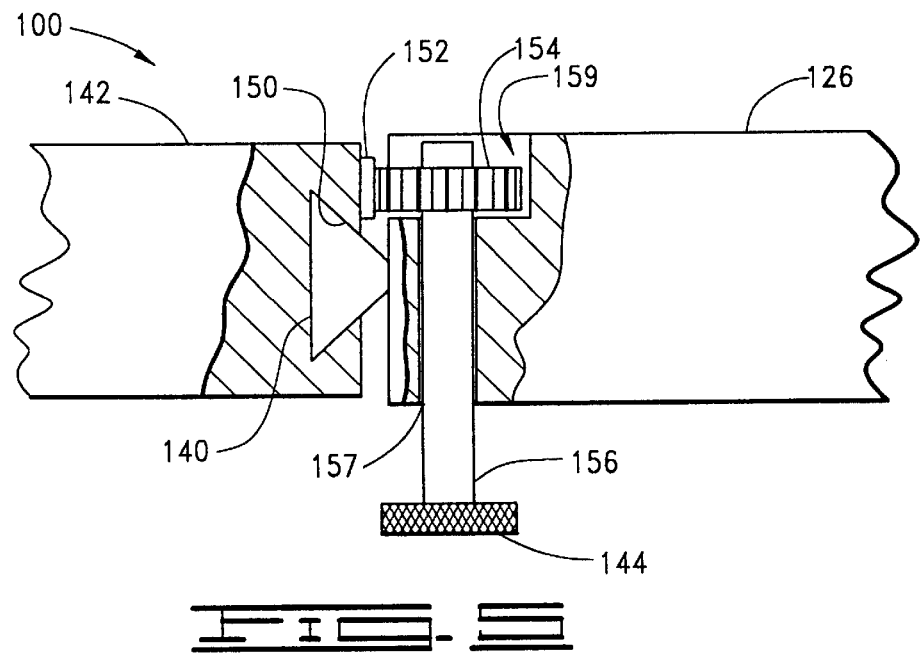
FIG. 5 a partial cross-sectional plan view of the support head and upper base of the impact tester of FIG. 1, showing in detail the geared connection there between for raising and lowering the support head of the impact tester.

FIG. 5 shows the upper base 126 and the support head 142, illustrating the manner in which the support head 142 forms a dovetail race 150 which matingly engages the slide 140. A gear rack 152 supported by the support head 142 matingly engages a pinion gear 154 which is supported by a shaft 156 extending through a bore 157 in the upper base 126, the pinion gear 154 disposed in an enlarged recess portion 159 of the bore 157. The shaft 156 is rotationally supported within the bore 157 in a conventional manner as is well known to one skilled in the art, such as by a bearing or bushing (not shown). Rotation of the knob 144 will impart rotation to gear 154 which, in turn, imparts linear displacement to gear 152. Thus, the support head 142 can be raised or lowered by turning the knob 144. The support head 142 may be supported in a selected vertical position by the frictional forces between the slide 140 and the race 150, and between the gear 152 and the gear 154. Alternatively, the support head 142 may be lockingly supported in a conventional manner by a set screw or locking screw (not shown).

Returning now to FIG. 1, it will be noted that the support head 142 supports a tubular wand 158 which has an axially disposed central passage (not shown). A vacuum line 160 is connected to the upper end of the wand 158 to provide a conduit for delivery of a vacuum from a conventional vacuum source such as a vacuum pump (not shown). A needle 162 having an annular cross-section is supported at the lower end of the wand 158, the needle 162 forming a central passage coextensive and contiguous to the central passage of the wand 158. Thus, a vacuum applied to the vacuum line 160 is transmitted through the wand 158 and through the needle 162. FIG. 3 shows an impact test ball 164 supported against the needle 162 by sealing engagement of the ball 164 against the needle 162 in cooperation with the vacuum applied by line 160. In this manner the ball 164 is said to be loaded into the ball drop fixture assembly 106. The ball 164 has a diameter of less than 1 millimeter.

Figure 6:
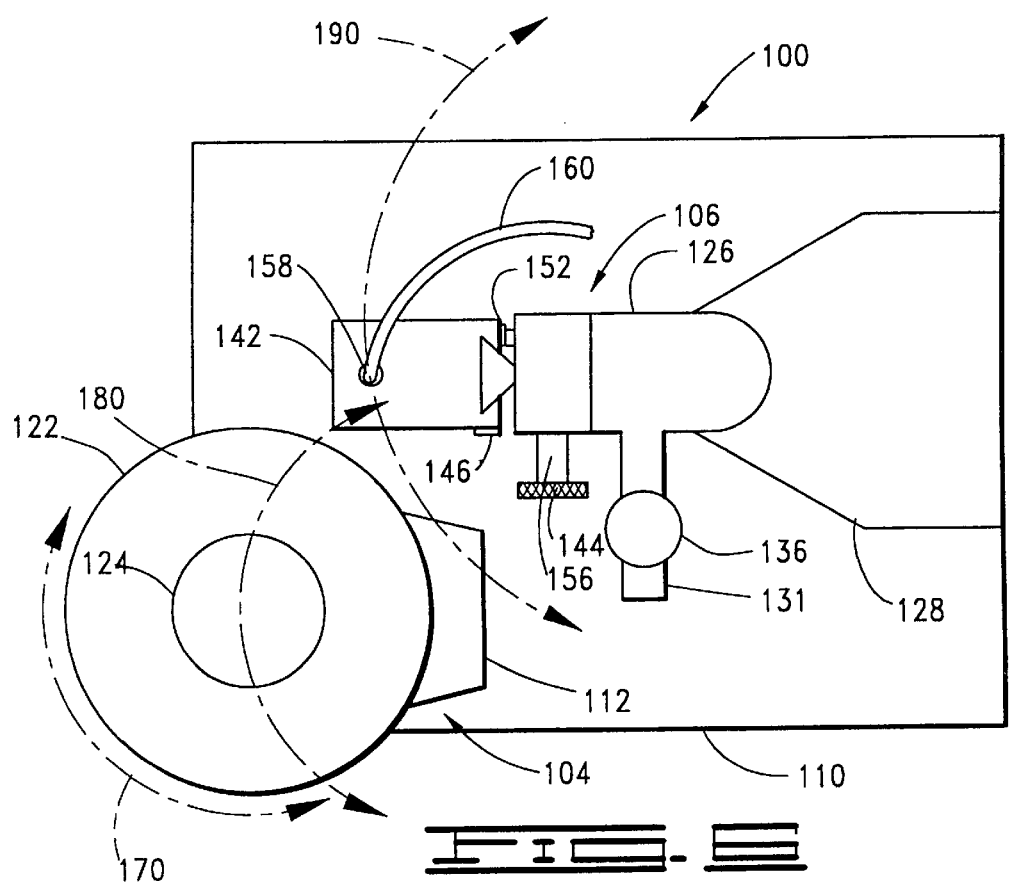
FIG. 6 is a plan view of the impact tester of FIG. 1.

A vacuum release valve 166, such as a spring biased ball or disc valve, is provided in the wand 158. The valve 166 is normally closed thereby sealing the wand 158 central passageway and maintaining the vacuum therein. Switching the valve 166 to an open position provides fluid communication of atmospheric pressure into the central passage of the wand 158, thereby effectively negating the vacuum in the needle 162. Negating the vacuum in this manner causes release of the support by the ball drop fixture assembly 106, subjecting the ball 164 to the opposing gravitational force. The minimal cross sectional contact of the needle 162 minimizes the tendency of the ball 164 to stick to the needle 162 resulting from stiction or debris. The impact test of the present invention is thus initiated by opening the valve 166 to cause the ball 164 to drop onto the target disc 122. FIG. 6 illustrates three degrees of freedom in positioning the target disc 122 under the wand 158. Rotation of the target disc 122, denoted by the arrowed broken line 170, is provided by the bearing assembly 114 (shown in FIG. 1). Articulation of the disc holder assembly 104 along the path 180 is provided by the journalled connection of the platform 110 and the swivel plate 112 by the bearing assembly 120 (shown in FIG. 2). Articulation of the ball drop fixture assembly 106 along the path 190 is provided by the journalled connection of the upper base 126 and the lower base 128 by the bearing assembly 130 (shown in FIG. 4).

In operation, the disc holder assembly 104 and the ball drop fixture assembly 106 are cooperatively positioned so as to place a desired radial portion of the target disc 122 under the wand 158. A discrete test location within a given radial portion is selected by rotating the disc plate 116. With the ball drop fixture assembly at a relatively high position to facilitate access, the vacuum source is activated and the ball 164 is loaded against the needle 162. The ball drop fixture assembly is next lowered in near proximity to the desired drop height and the ball drop fixture assembly 106 position is locked by turning the knob 136 to rotate the shaft 134 such that the brake 138 is caused to pressingly engage the platform 110. With the ball 164 loaded for dropping, the final height adjustment is achieved by raising or lowering the support head 142 by turning the knob 144.

The valve 166 is switched to an open position to release the vacuum grip on the ball 164, causing the ball 164 to impact the target disc 122. The impact of the falling ball 164 creates a detent in the target disc 122. The characteristics of the detent, in contemplation of the ball and drop height, are compared to analytical standards, empirically derived from baseline testing, which indicate the dynamic hardness of the target disc at the location tested.

The following table illustrates a summary of the observed differences between discs received from two suppliers of magnetic media, the observations made with the tester of the present invention using a 0.5 mm diameter tungsten carbide ball. It will be clear to one skilled in the art that observations such as those of Table 1 require the use of high resolution surface profiling instruments such as a stylus profilometer, an interferometer or an atomic force microscope.

TABLE 1

| Average Detent Depth (Angstroms) | | |
|---|---|---|
| Drop Height (mm) | Supplier A | Supplier B |
| 3 | 221 | 142 |
| 5 | 425 | 172 |
| 10 | 883 | 459 |
| 25 | 2022 | 1208 |

The Table 1 summary illustrates that a measurable difference existed in the depth of detents observed in material supplied by Supplier A as opposed to that of Supplier B. The depth of the detent is an observable characteristic that is indicative of the material's dynamic hardness. The shallower depths in Supplier B's material indicates a harder surface that is correspondingly more resistant to mechanical failure.

Although Table 1 only shows average values from numerous trials, one skilled in the art will recognize that statistical evaluations of the distribution of individual readings provide probability curves that can be used to empirically establish acceptability limits for incoming batches of material. Baseline testing of discs of known hardness can furthermore be subjected to functional testing to establish a correlation between hardness and reliability, thus deriving minimum acceptable hardness for incoming batches of material.

Other observable impact response characteristics in addition to detent depth are indicative of the material's mechanical properties, such as the amount of debris located in and around the detent, and the number and size of any cracks and delaminations in the detent area. These characteristics, typically hundreds of angstroms in dimension, can be quantified using a high resolution instrument such as an atomic force microscope, and used to determine a batch's acceptability based on empirically determined limits.

It should be noted that, with the impact tester 100 described herein, by varying drop height or ball material (that is, ball material density and therefore impact energy), it is possible to probe thin layered structures to check mechanical properties of different layers.

Figure 7:
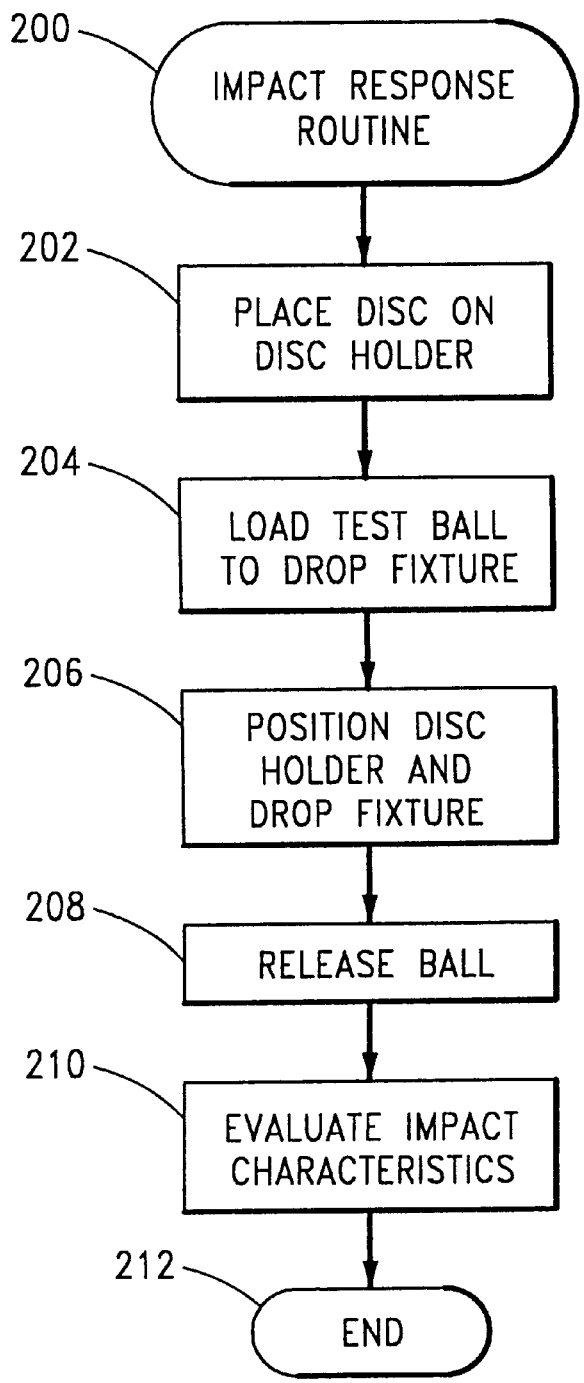
FIG. 7 is a process flow chart of the operation of the impact tester in accordance with a preferred embodiment of the present invention.

FIG. 7 illustrates the method of the present invention as described above in testing a magnetic disc to characterize its impact response as outlined in blocks 200–212. Beginning with block 202, the disc is initially supported on the disc plate 116 of the disc holder assembly 104, as illustrated in FIG. 3. The test ball 164 is loaded to the ball drop fixture assembly 106, block 209, by placing the test ball 164 adjacent the needle 162 which communicates the suction pressure of the vacuum source to the test ball 164. Block 206 shows that the ball drop fixture assembly 106 and the disc holder assembly 104 are cooperatively positioned to place the selected test position of the target disc 122 below the test ball 164. Next, the test ball 164 is released by opening the vacuum release valve 166, as indicated by block 208. Once the test ball has impacted the target disc 122, the characteristics of the impact response of the target disc 122 are evaluated at block 210.

Accordingly, in view of the foregoing it will be recognized that the present invention is directed to an apparatus and method for characterizing impact response of a material, such as a disc 122 of a disc drive. A base (such as 102) is provided to support a material holder (such as 104) and a ball drop fixture (such as 106), the material holder supporting a test ball (such as 164) by way of a vacuum source (such as 160) that provides a suction pressure. A vacuum release valve (such as 166) is employed to negate the suction pressure, thereby releasing the ball to impact the material.

It is to be understood that even though numerous characteristics and advantages of various embodiments of the present invention have been set forth in the foregoing description, together with details of the structure and function of various embodiments of the invention, this disclosure is illustrative only, and changes may be made in details especially in matters of structure and arrangement of parts within the principles of the present invention to the full extent indicated by the broad general meaning of the terms in which the appended claims are expressed. For example, the particular elements may vary depending on the particular application for the impact tester while maintaining substantially the same functionality without departing from the scope and spirit of the present invention.

In addition, although the preferred embodiment described herein is directed to an impact tester for testing disc drive discs, it will be appreciated by those skilled in the art that the teaching of the present invention can be applied to other materials as well, such as thin and thick films, layered structures or other materials whose near-surface mechanical impact properties need to be probed, without departing from the scope and spirit of the present invention.

It is clear that the present invention is well adapted to attain the ends and advantages mentioned as well as those inherent therein. While a presently preferred embodiment of the invention has been described for purposes of the disclosure, it will be understood that numerous changes may be made which will readily suggest themselves to those skilled in the art and which are encompassed within the spirit of the invention disclosed and as defined in the appended claims.

What is claimed is:

1. A method of characterizing the impact response of a disc, comprising steps of:

(a) placing the disc on a material support;

(b) providing a vacuum to an open-ended test ball support to impart a suction pressure to the open end of the ball support;

(c) placing a test ball abuttingly adjacent the ball support open end, whereby the suction pressure to the open end of the ball support;

(d) positioning the ball support and cooperatively positioning the material support so that the test ball is positioned no more than 10 millimeters above a desired target location on the disc;

(e) venting positive pressure to the ball support to negate the suction pressure, causing the test ball to fall onto the disc to effect a detent thereon; and (f) evaluating the microscopic depth of the detent through use of a high power microscope to characterize the impact response of the disc.

2. An apparatus for characterizing impact response of a disc of a disc drive assembly, the apparatus comprising a base wherein; the base comprises a platform and the ball drop fixture further comprises a fixture base having a first end pivotally supported by said platform so as to provide articulation of a second end of said fixture base in substantially parallel relation to said platform; wherein the fixture base further comprises:

a slide supported by said fixture base second end;

a support head matingly engaging said slide and vertically positionable thereon relative to said fixture base second end;

a gear rack supported by said support head;

a pinion gear supported by said fixture base second end and engaging said gear rack, rotation of said pinion gear imparting vertical displacement to said support head; and a shaft depending from said gear, rotation of said shaft effecting vertical displacement of the test ball supported by said wand to permit vertical positioning of the test ball to a desired height above the target disc.

3. The apparatus of claim 2 wherein the test ball is characterized as being spherical and having a diameter smaller than about one millimeter.

4. An apparatus for characterizing impact response of a disc of a disc drive assembly, the apparatus comprising:

a base having a platform;

a material holder, supported by the base, which supports the disc;

a ball drop fixture, supported by the base and operably connected to a vacuum source which provides a suction pressure, which supports a test ball above the disc, wherein the material holder adjustably positions a desired target location on the disc under the test ball, the ball drop fixture comprising:

a fixture base comprising:

a slide supported by said fixture base;

a support head matingly engaging said slide and vertically positionable thereon relative to said fixture base;

a gear rack supported by said support head;

a pinion gear supported by said fixture base and engaging said gear rack, rotation of said pinion gear imparting vertical displacement to said support head; and a shaft depending from said gear, rotation of said shaft effecting vertical displacement of the test ball supported by said wand to permit vertical positioning of the test ball to a desired height above the target disc; and a vacuum release valve which negates the suction pressure so as to release the support of the test ball from the ball drop fixture.

5. The apparatus of claim 4 wherein said fixture base further comprises a lock to prevent relative movement of the fixture base relative the platform at any one of a plurality of articulated positions of said fixture base.

* * * * *